United States Patent
Reel et al.

(10) Patent No.: US 8,765,960 B2
(45) Date of Patent: Jul. 1, 2014

(54) 6-((S)-1-{1-[5-(2-HYDROXY-ETHOXY)-PYRIDIN-2-YL]-1H-PYRAZOL-3-YL}-ETHYL)-3H-1,3-BENZOTHIAZOL-2-ONE AS A TARP-GAMMA 8 DEPENDENT AMPA RECEPTOR ANTAGONIST

(71) Applicant: Eli Lilly and Company, Indianapolis, IN (US)

(72) Inventors: Jon Kevin Reel, Carmel, IN (US); Warren Jaye Porter, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/084,683

(22) Filed: Nov. 20, 2013

(65) Prior Publication Data

US 2014/0148441 A1 May 29, 2014

Related U.S. Application Data

(60) Provisional application No. 61/730,273, filed on Nov. 27, 2012.

(51) Int. Cl.
*C07D 417/14* (2006.01)
*A61K 31/4439* (2006.01)
*A61K 45/06* (2006.01)

(52) U.S. Cl.
USPC ............. 546/270.1; 514/217; 514/338

(58) Field of Classification Search
None
See application file for complete search history.

(56) References Cited

FOREIGN PATENT DOCUMENTS

| EP | 1300396 A1 | 4/2003 | | |
|---|---|---|---|---|
| WO | 2007/076161 A2 | 7/2007 | | |
| WO | WO2007/076161 | * | 7/2007 | ............ A61K 31/422 |
| WO | WO2011/153192 | * | 12/2011 | ............ C07D 417/04 |

OTHER PUBLICATIONS

Michael A. Rogawski, "Revisiting AMPA Receptors as an Antiepileptic Drug Target", Epilepsy Currents, vol. 11, No. 2 (Mar./Apr.) 2011 pp. 56-63.
Martin B Gill and David S Bredt, "An Emerging Role for TARPs in Neuropsychiatric Disorders", Neuropsychopharmacology Reviews (2011) 36, pp. 362-363.
Timothy Gross, Shine Chou, Alan Dyke, Beatriz Dominguez, Michelle Groarke, Jonathan Medlock, Michael Ouellette, Jayachandra P. Reddy, Andreas Seger, Scott Zook, Antonio Zanotti-Gerosa, "Application of [BoPhoz Fh] catalysts in the asymmetric hydrogenation of a pyridyl benzothiophene alkene" Tetrahedron Letters (2012) 53, pp. 1025-1028.
Xiang Wang,* Anil Guram, Seb Caille, Jack Hu, J P. Preston, Michael Ronk and Shawn Walker, "Highly Enantioselective Hydrogenation of Styrenes Directed by 2'-Hydroxyl Groups" Organic Letters (2011) vol. 13, No. 7, pp. 1881-1883.
Borut Zupancic, Barbara Mohar and Michel Stephan, "Heavyweight "R-SMS-Phos" Ligands in the Olefins' Hydrogenation Arena" Organic Letters (2010) vol. 12, No. 6, pp. 1296-1299.

* cited by examiner

*Primary Examiner* — Dennis Heyer
(74) *Attorney, Agent, or Firm* — R. Craig Tucker

(57) ABSTRACT

A TARP γ8 dependant AMPA receptor antagonist of the formula:

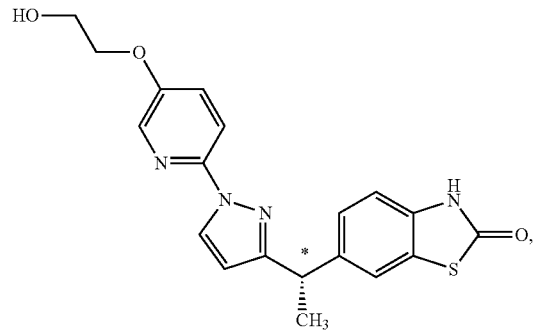

its pharmaceutically acceptable salts, uses, and methods for its preparation are described.

13 Claims, No Drawings

6-((S)-1-{1-[5-(2-HYDROXY-ETHOXY)-PYRIDIN-2-YL]-1H-PYRAZOL-3-YL}-ETHYL)-3H-1,3-BENZOTHIAZOL-2-ONE AS A TARP-GAMMA 8 DEPENDENT AMPA RECEPTOR ANTAGONIST

This application claims priority to U.S. provisional application Ser. No. 61/730,273, filed Nov. 27, 2012.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA (γ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA (α-amino-3-hydroxyl-5-methyl-4-isoxazole-propionic acid) receptors are glutamate sensitive ion channels on postsynaptic membranes of excitatory synapses in the central nervous system and are largely responsible for mediating fast neurotransmission across synaptic gaps. AMPA receptor antagonists are known anticonvulsant agents and their ability to down modulate excitatory neurotransmission is key to their anti-epileptic therapeutic potential. However, since AMPA receptor activity is so ubiquitous in the CNS, general antagonism affects most areas of the CNS resulting in undesired effects, such as ataxia, sedation, and/or dizziness, which are shared by all known general AMPA receptor antagonists. Typically these general antagonists have very narrow therapeutic dosing windows, meaning that typically the doses needed to obtain anti-convulsant activity are close to or overlap with doses at which undesired effects are observed. (Michael A. Rogawski. "Revisiting AMPA Receptors as an Antiepileptic Drug Target" *Epilepsy Currents* 11.2 (2011).)

Transmembrane AMPA Receptor Regulatory Proteins (TARPs) are a fairly recently discovered family of proteins that have been found to associate with and modulate the activity of AMPA receptors. Several TARPs are fairly regiospecific in the brain, leading to physiological differentiation of the AMPA receptor activity. As for example, TARP γ2 (stargazin) dependent AMPA receptors are primarily localized in the cerebellum and cerebral cortex and TARP γ8 dependent AMPA receptors are localized primarily in the hippocampus, which region is particularly relevant to seizure origination and/or propagation. It has been theorized that targeting individual TARPs may enable selective modulation of specific brain circuits without globally affecting synaptic transmission. (Gill, Martin B. and Bredt, David S., Neuropsychopharmacology 36(1): 362-363 (2011).)

Levetiracetam ((S)-2-(2-oxopyrrolidin-1-yl)butanamide), gabapentin (2-[1-(aminomethyl)cyclohexyl]acetic acid), topiramate (2,3:4,5-Bis-O-(1-methylethylidene)-beta-D-fructopyranose sulfamate), and carbamazepine (5H-dibenzo[b,f]azepine-5-carboxamide) are current leading therapeutic drugs for epileptic seizures. None of the currently approved drugs appear to act entirely through modulation of AMPA receptors.

Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-quinazolin-3-yl]methanesulfonamide), and parampanel (5'-(2-cyanophenyl)-1'-phenyl-2,3'-bipyridinyl-6'(1'H)-one) are general (non-TARP dependent/non-selective) AMPA receptor antagonists being tested as anti-epileptics.

It is here suggested that a selective, non-competitive TARP γ8 dependent AMPA receptor antagonist could be an effective anti-seizure/anti-epiletic therapeutic without the side effects (e.g. sedation, ataxis, and/or dizziness) of general (non-TARP dependent/non-selective) AMPA antagonists or TARP γ2 dependent AMPA antagonists, which are more associated with AMPA receptor antagonism in the cerebellum.

The present invention provides a compound which displays potent and selective TARP γ8-dependent AMPA receptor antagonist activity in vitro, as well as efficacy in animal models of seizure and pain. Thus, the present invention provides a compound which is believed to be useful for the treatment of seizures in patients with epilepsy, as for example simple and/or complex partial onset seizures, and/or primary and/or secondary generalized seizures. Further, the compound of the invention may also be useful in the treatment of pain. More, particularly, the present invention provides the compound of Formula I

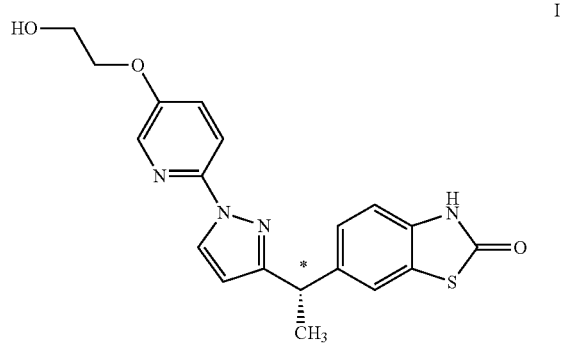 [SMILES: C[C@@H](c1ccc2[nH]c(=O)sc2c1)c1ccn(-c2ccc(OCCO)cn2)n1]

(i.e. 6-((S)-1-{1-[5-(2-hydroxy-ethoxy)-pyridin-2-yl]-1H-pyrazol-3-yl}-ethyl)-3H-1,3-benzothiazol-2-one), or a pharmaceutically acceptable salt thereof.

In another aspect of the invention there is provided a pharmaceutical composition comprising the compound of Formula I, or a pharmaceutically acceptable salt thereof, and one or more pharmaceutically acceptable carriers, diluents, or excipients. Furthermore, this aspect of the invention provides a pharmaceutical composition for treating seizures, as for example simple and/or complex partial onset seizures, and/or primary and/or secondary generalized seizures, in patients with epilepsy, comprising the compound of Formula I, or a pharmaceutically acceptable salt thereof, and one or more pharmaceutically acceptable excipients, carriers, or diluents. Further, this aspect of the invention provides a pharmaceutical composition comprising the compound of Formula I, or a pharmaceutically acceptable salt thereof, a second therapeutic agent which is an antiepileptic drug, as for example levetiracetam, gabapentin, topiramate, or carbamazepine, and one or more pharmaceutically acceptable carriers, diluents, or excipients.

The present invention also provides a method of treating seizures, as for example simple and/or complex partial onset seizures, and/or primary and/or secondary generalized seizures, in a mammal with epilepsy, comprising administering to a mammal in need of such treatment an effective amount of the compound of Formula I, or a pharmaceutically acceptable salt thereof. In another embodiment of this aspect of the invention, the method further comprises administering in simultaneous, separate or sequential combination, a second therapeutic agent which is an antiepileptic drug, as for example levetiracetam, gabapentin, topiramate, or carbamazepine. In one particular embodiment of these methods of treatment, the mammal is a human.

This invention also provides the compound of Formula I, or a pharmaceutically acceptable salt thereof for use in therapy. Within this aspect, the invention provides the compound of Formula I, or a pharmaceutically acceptable salt thereof, for use in the treatment of seizures, as for example simple and/or complex partial onset seizures, and/or primary and/or secondary generalized seizures, in a mammal, particularly a human, with epilepsy. Further, this aspect of the invention provides the compound of Formula I, or a pharmaceutically acceptable salt thereof, for use in simultaneous, separate or sequential combination with an antiepileptic drug, as for example levetiracetam, gabapentin, topiramate, or carbamazepine, in the treatment of seizures in a mammal, particularly a human, with epilepsy.

Another aspect of this invention provides the use of the compound of Formula I, or a pharmaceutically acceptable salt thereof, in the manufacture of a medicament for the treatment of seizures, as for example simple and/or complex partial onset seizures, and/or primary and/or secondary generalized seizures, in a mammal, particularly a human, with epilepsy. Further, the invention provides the use of the compound of Formula I, or a pharmaceutically acceptable salt thereof, in the manufacture of a medicament for the treatment of seizures, as for example simple and/or complex partial onset seizures, and/or primary and/or secondary generalized seizures, in a mammal, particularly a human, with epilepsy, wherein said medicament is to be adminstered in simultaneous, seperate or sequential combination with a second therapeutic agent which is an antiepileptic drug, as for example levetiracetam, gabapentin, topiramate, or carbamazepine.

Yet another aspect of the invention provides for a pharmaceutical composition for treating pain, comprising the compound of Formula I, or a pharmaceutically acceptable salt thereof, and one or more pharmaceutically acceptable excipients, carriers, or diluents.

Another aspect of the invention provides a method of treating pain in a mammal comprising administering to a mammal in need of such treatment an effective amount of the compound of Formula I, or a pharmaceutically acceptable salt thereof. In one particular embodiment of this method of treatment, the mammal is a human.

Another aspect of the invention provides the compound of Formula I, or a pharmaceutically acceptable salt thereof, for use in the treatment of pain, particularly in a human.

Another aspect of this invention provides the use of the compound of Formula I, or a pharmaceutically acceptable salt thereof, in the manufacture of a medicament for the treatment of pain.

Compounds of this invention have basic and acidic moieties, and accordingly react with a number of organic and inorganic acids and bases to form pharmaceutically acceptable salts. Pharmaceutically acceptable salts of the compound of the present invention are contemplated within the scope of the present application. The term "pharmaceutically acceptable salt" as used herein, refers to any salt of the compound of the invention that is substantially non-toxic to living organisms. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); and S. M. Berge, et al., "Pharmaceutical Salts", *Journal of Pharmaceutical Sciences*, Vol 66, No. 1, January 1977.

Abbreviations used herein are defined as follows:
"AMPA" means α-amino-3-hydroxyl-5-methyl-4-isoxazole-propionic acid.
"Brine" means saturated NaCl.
"CHO" means Chinese hamster ovary.
"CTZ" means cyclothiazide.
"DCM" means dichloromethane.
"DMEM means Dulbecco's Minimum Eagle's Medium.
"DMSO" means dimethyl sulfoxide (perdeuterated [d6] if for NMR).
"$ED_{50}$" means the dose that produces the 50% of the maximum effect observed.
"Eq" means molar equivalent.
"EtOAc" means ethyl acetate.
"EtOH" means ethanol.
"FLIPR" means fluorescence imaging plate reader.
"HBSS" means Hank's Buffered Salt Solution.
"HEPES" means 4-(2-hydroxyethyl)-1-piperazine ethanesulfonic acid.
"HPLC" means high pressure liquid chromatography.
"hr." or "h" means hour or hours.
"$IC_{50}$" means the concentration at which 50% of the maximum inhibition is achieved.
"LCMS" means liquid chromatography mass spectrometry.
"MeOH" means methanol.
"min" or "m" means minutes.
"MS" means mass spectroscopy or mass spectrum.
"p.o." means per os, by mouth.
"PTZ" means pentylenetetrazole.
"RT" means retention time.
"S.C." means subcutaneous.
"SEM" means standard error of the mean.
"TARP" means Transmembrane AMPA Receptor Regulatory Protein.
"THF" means tetrahydrofuran.
"VCD" means vibrational circular dichroism.
"XRPD" means x-ray powder diffraction.

GENERAL CHEMISTRY

The compound of the present invention can be prepared by general methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical.

In the following illustrative preparations and examples, solvents are generally removed under reduced pressure (evaporated). In some procedures indicated yields are representative crude yields for products which are isolated by evaporation or filtration and used directly without further purification.

Preparation 1: 6-Acetyl-3-(methoxymethyl)-3H-1,3-benzothiazol-2-one

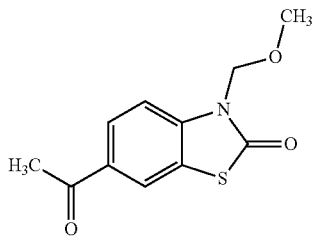 [SMILES: COCn1c(=O)sc2cc(C(C)=O)ccc21]

Add cesium carbonate (1.5 Eq; 310.5 mmoles; 101.1 g) to a solution of 6-acetyl-3H-1,3-benzothiazol-2-one (40.0 g, 207 mmoles) in dimethylformamide (690 mL). Add chloromethyl methyl ether (1.3 Eq, 269 mmoles, 20.4 mL) dropwise and stir at room temperature for 18 hr. Transfer to a separatory funnel, add EtOAc (1 L), wash with water (2×200 mL), and then brine (200 mL). Back extract with DCM (300 mL). Dry the combined organic layers over $Na_2SO_4$, filter and concentrate. Slurry the concentrate in 200 ml hexanes/EtOAc (75: 25), and filter to give 6-acetyl-3-(methoxymethyl)-3H-1,3-benzothiazol-2-one as a white solid (37.0 g, 156 mmoles, 75% yield). LCMS (low) rt=1.68 min., M+1=238.

Preparation 2: 6-[1-Hydroxy-1-(1-tetrahydropyran-2-yl-1H-pyrazol-5-yl)ethyl]-3-(methoxymethyl)-3H-1,3-benzothiazol-2-one (Racemic Mixture of Diasteromers)

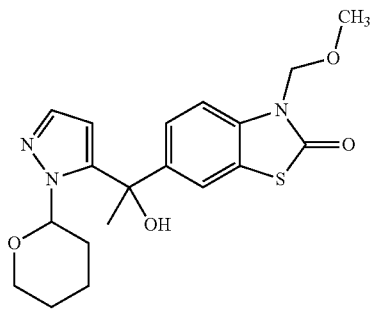 [SMILES: COCn1c(=O)sc2cc(C(C)(O)c3ccnn3C3CCCCO3)ccc21]

Add 1-tetrahydropyran-2-yl-pyrazole (1.5 Eq, 202 mmoles, 30.8 g)(Aldrich) and THF (900 mL) to a flame dried 2 L 3 neck round bottom flask and cool to −78° C. (dry ice/acetone bath). Add t-butyl lithium (2.5 M in THF)(1.5 Eq, 202 mmoles; 81.0 mL) dropwise, maintaining at least −68° C., and stir for 60 min at −78° C. Add a solution of 6-acetyl-3-(methoxymethyl)-3H-1,3-benzothiazol-2-one (32.0 g, 134 mmoles) in THF (450 mL) dropwise over 45 min, and stir at −78 for 30 min. Remove the dry ice bath and allow to warm to −50° C. and stir for 1 hr. (do not let temp. rise above −45° C.). Quench the reaction with MeOH (80 mL). Transfer to a separatory funnel, add EtOAc (2000 mL), and wash with water (500 mL) and then brine (500 mL). The organic layer is dried over $Na_2SO_4$, filter and concentrate to give a crude yellow oil. Purify the material by HPLC, eluting with hexanes/EtOAc (6:4) to yield 6-[1-hydroxy-1-(1-tetrahydropyran-2-yl-1H-pyrazol-5-yl)ethyl]-3-(methoxymethyl)-3H-1,3-benzothiazol-2-one as a white foam (44 g, 113 mmoles, 84% yield) (Racemic mixture of diasteromers). LCMS (Low) rt=1.76 min., M+1=288, and rt=1.86 min., M+1=288

Preparation 3: 3-(Methoxymethyl)-6-[1-(1H-pyrazol-5-yl)ethenyl]-3H-1,3-benzothiazol-2-one

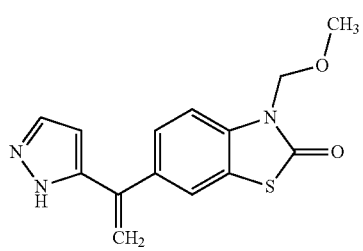 [SMILES: C=C(c1ccc2c(c1)sc(=O)n2COC)c1ccn[nH]1]

Add trifluoroacetic acid (20 Eq (molar), 2.26 moles, 170 mL) to a solution of 6-[1-hydroxy-1-(1-tetrahydropyran-2-yl-1H-pyrazol-5-yl)ethyl]-3-(methoxymethyl)-3H-1,3-benzothiazol-2-one (44 g, 113 mmoles) in DCM (0.2 M, 8.81 moles, 565 mL) and stirr at room temperature over night (~16 hr.). Concentrate the resulting dark purple reaction mixture, dissolve it in EtOAc (2 L) and neutralize the solution by slowly adding saturated aqueous sodium bicarbonate. Transfer to a separatory funnel and extract into EtOAc, wash with water (300 mL) and then brine (300 mL). Dry over $Na_2SO_4$, filter, and concentrate. Purify the material by HPLC, eluting with EtOAc/Hexanes (1:1) to give 3-(methoxymethyl)-6-[1-(1H-pyrazol-5-yl)ethenyl]-3H-1,3-benzothiazol-2-one (30 g, 104 mmoles, 92% yield) as a thick yellow oil. LCMS (Low) desired product peak at rt=1.82 min., M+1=288.

Preparation 4: 3-(Methoxymethyl)-6-[1-(1H-pyrazol-5-yl)ethyl]-3H-1,3-benzothiazol-2-one

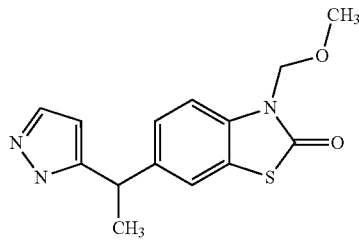 [SMILES: COCn1c(=O)sc2cc(C(C)c3ccn[nH]3)ccc21]

Add 5% palladium/carbon (15 g; 7.0 mmoles) to a $N_2$ purged flask and add EtOAc (250 mL). Add 3-(methoxymethyl)-6-[1-(1H-pyrazol-5-yl)ethenyl]-3H-1,3-benzothiazol-2-one (29 g, 101 mmoles) as a solution in EtOAc (250 mL). Degas under vacuum and charge with hydrogen via balloon. Stir overnight, evacuate excess hydrogen under pressure and flush with $N_2$. Filter through diatomaceous earth and concentrate to give 3-(methoxymethyl)-6-[1-(1H-pyrazol-5-yl)ethyl]-3H-1,3-benzothiazol-2-one as a thick yellow oil (27 g, 93 mmoles; 92% yield). Material may be carried into the next step without further purification. LCMS (Low) rt=1.73 min., M+1=290.

Preparation 5: 2-Fluoro-5-[2-(tetrahydro-2H-pyran-2-yloxy)ethoxy]pyridine

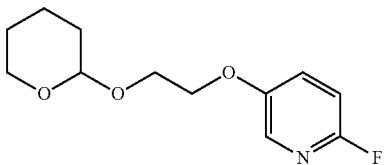 [SMILES: Fc1ccc(OCCOC2CCCCO2)cn1]

Add cesium carbonate (3 Eq, 53.05 mmoles; 17.2 g) to a solution of 2-fluoro-5-hydroxypyridine (2.0 g, 1.00 Eq, 17.68 mmoles) in dimethylformamide (0.3 M; 762.37 mmoles; 59.0 mL), followed by 2-(2-bromoethoxy)tetrahydro-2H-pyran (17.7 mmoles, 3.7 g) and stir at room temperature overnight. Transfer to a separatory funnel and add EtOAc (500 mL). Wash organic layer, wash with water (300 mL) followed by brine (200 mL). Dry over Na₂SO₄, filter and concentrate. Purify the crude mixture by HPLC eluting with hexanes/EtOAc 7/3 to give 2-fluoro-5-[2-(tetrahydro-2H-pyran-2-yloxy)ethoxy]pyridine as a pale yellow oil (3.9 g, 16.2 mmoles; 91% yield). LCMS (Low) rt=1.8 min., M+1=242.

Preparation 6: 3-(Methoxymethyl)-6-{1-[1-(5-{2-(tetrahydro-2H-pyran-2-yloxy)ethoxy}pyridine-2-yl)-1H-pyrazol-3-yl]ethyl}-3H-1,3-benzothiazol-2-one (Racemic Mixture of Diasteromers)

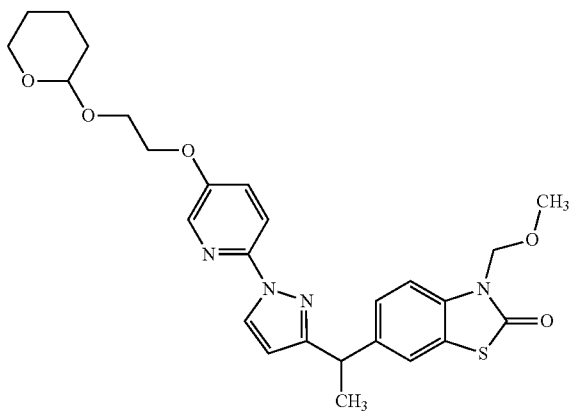 [SMILES: COCn1c(=O)sc2cc(C(C)c3ccn(-c4ccc(OCCOC5CCCCO5)cn4)n3)ccc21]

Dissolve 3-(methoxymethyl)-6-[1-(1H-pyrazol-5-yl)ethyl]-3H-1,3-benzothiazol-2-one (7.7 g, 26.6 mmoles) in dimethylformamide (0.2 M; 133 mL). Add lithium t-butoxide ((1.5 Eq of a 1.00 molar solution in THF), 39.9 mmoles; 39.9 mL)) and stir 15 min. Add 2-fluoro-5-[2-(tetrahydro-2H-pyran-2-yloxy)ethoxy]pyridine (2.00 Eq; 53.2 mmoles; 12.8 g). Heat the reaction in an oil bath to 140° C. and purge with N₂ to remove THF. Heat the mixture at reflux for 5 hr. Cool the mixture to room temperature and quench with saturated ammonium chloride. Extract into EtOAc (2×200 mL), wash with water (2×100 mL), followed by brine (200 mL). Dry over sodium sulfate, filter and concentrate. Purify by HPLC (silica) eluting with 40% EtOAc/hexanes to give 3-(methoxymethyl)-6-{1-[1-(5-{2-(tetrahydro-2H-pyran-2-yloxy)ethoxy}pyridine-2-yl)-1H-pyrazol-3-yl]ethyl}-3H-1,3-benzothiazol-2-one as a pale yellow oil (10 g; 19.6 mmoles, 74% yield). LCMS (low) rt=2.6, M+1=511.

Example 1

6-(1-{1-[5-(2-hydroxy-ethoxy)-pyridin-2-yl]-1H-pyrazol-3-yl}-ethyl)-3H-1,3-benzothiazol-2-one, Racemate

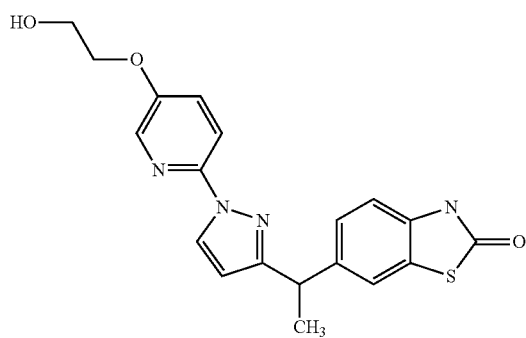

Dissolve 3-(methoxymethyl)-6-{1-[1-(5-{2-(tetrahydro-2H-pyran-2-yloxy)ethoxy}pyridine-2-yl)-1H-pyrazol-3-yl]ethyl}-3H-1,3-benzothiazol-2-one (140 mg, 274.18 µmoles) in trifluoroacetic acid (0.05 M; 73 mmoles; 5.5 mL) and heat at reflux (~72° C.) under N₂ for 2 hr. (orange color observed after about 10 min. and at 70° C.). Cool the reaction to room temperature and concentrate under reduced pressure. Dissolve the residue in THF (0.05 M; 67 mmoles, 5.5 mL), add 28% ammonium hydroxide (0.2 M; 9.9 mmoles; 1.4 mL), and stir at room temperature for ~1 hr. Dilute with EtOAc (100 ml), wash with brine, dry over sodium sulfate, filter and concentrate. Purify by liquid chromatography on a 25 g silica gel column, eluting with a gradient of 60-80% EtOAc in hexanes to give 6-(1-{1-[5-(2-hydroxy-ethoxy)-pyridin-2-yl]-1H-pyrazol-3-yl}-ethyl)-3H-1,3-benzothiazol-2-one as a white foam (80 mg; 209 µmoles; 76% yield). LCMS (Low) rt 1.8 min., M+1=383.

Example 2

6-((S)-1-{1-[5-(2-hydroxy-ethoxy)-pyridin-2-yl]-1H-pyrazol-3-yl}-ethyl)-3H-1,3-benzothiazol-2-one (Isomer 1)

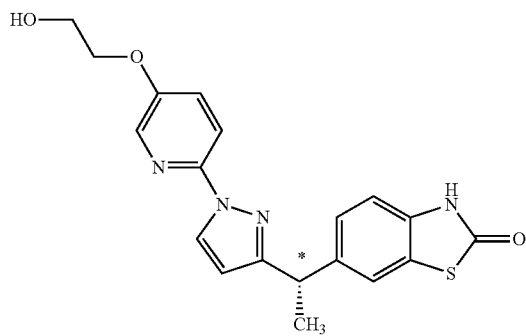 [SMILES: C[C@@H](c1ccc2[nH]c(=O)sc2c1)c1ccn(-c2ccc(OCCO)cn2)n1]

Dissolve 6-(1-{1-[5-(2-hydroxy-ethoxy)-pyridin-2-yl]-1H-pyrazol-3-yl}-ethyl)-3H-1,3-benzothiazol-2-one (330 mg) in MeOH (3.0 mL) and DCM (2.5 mL) and resolve into enantiomers by chiral chromatography using Chiralcel® OJ-H (2.1×15 cm, 5 μm column, Chiral Technologies Europe), eluting with 40% MeOH/liquid $CO_2$, 70 mL/min., detecting at 225 nm, injecting 300 μl, aliquots per run. Fractions containing the separated enantiomers are combined and concentrated under vacuum to afford Isomer 1 (150 mg) and Isomer 2 (169 mg) as amorphous white solids. Analytical chiral chromatography using Chiracel® OJ-H (4.6×150 mm, 5 μm column, Chiral Technologies Europe), eluting with 40% MeOH/liquid $CO_2$, 5 mL/min., detecting at 225 nm, characterized Isomer 1 with rt=2.03 min. and Isomer 2 with rt=2.66 min. LCMS (Low): Isomer 1 rt 1.8 min., M+1=383; Isomer 2, rt 1.8 min., M+1=383.

Crystallization: Form I:

6-((S)-1-{1-[5-(2-Hydroxy-ethoxy)-pyridin-2-yl]-1H-pyrazol-3-yl}-ethyl)-3H-1,3-benzothiazol-2-one (Isomer 1)(56.9 mg) is dissolved in 1:1 EtOH:heptane (3.0 mL), stirring for 20 min at 70° C. The solution is filtered while hot and split into two equal portions; one of which is transferred to a vial at ambient temperature, capped and stirred overnight at 5° C. The solids are recovered by filtration and dried under nitrogen to give crystal Form I (23.9 mg, 84% yield).

Absolute stereochemistry for Isomer I is confirmed to be 6-((S)-1-{1-[5-(2-Hydroxy-ethoxy)-pyridin-2-yl]-1H-pyrazol-3-yl}-ethyl)-3H-1,3-benzothiazol-2-one by single crystal x-ray crystallography.

X-Ray Powder Diffraction

The XRPD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U.S. Pharmacopeia 33—National Formulary 28 Chapter <941> Characterization of Crystalline Solids by X-ray Powder Diffraction (XRPD) Official Oct. 1, 2010-Feb. 1, 2011. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

6-((S)-1-{1-[5-(2-Hydroxy-ethoxy)-pyridin-2-yl]-1H-pyrazol-3-yl}-ethyl)-3H-1,3-benzothiazol-2-one (Isomer 1) is characterized by an XRPD pattern using CuKa radiation as having diffraction peaks (2-theta values) as described in Table 1 below. Specifically the pattern contains a peak at 15.81 in combination with one or more of the peaks selected from the group consisting of 16.62, 14.39, 14.05, 11.54 and 10.99 with a tolerance for the diffraction angles of 0.2 degrees.

TABLE 1

X-ray powder diffraction peaks of 6-((S)-1-{1-[5-(2-Hydroxy-ethoxy)-pyridin-2-yl]-1H-pyrazol-3-yl}-ethyl)-3H-1,3-benzothiazol-2-one (Isomer 1) Form 1.

| Peak | Angle (2-Theta °) | Intensity (%) |
|---|---|---|
| 1 | 5.44 | 8 |
| 2 | 7.85 | 21 |
| 3 | 10.99 | 44 |
| 4 | 11.54 | 34 |
| 5 | 14.05 | 75 |
| 6 | 14.39 | 26 |
| 7 | 15.81 | 100 |
| 8 | 16.62 | 27 |
| 9 | 20.22 | 8 |
| 10 | 21.61 | 16 |
| 11 | 22.69 | 8 |
| 12 | 23.41 | 14 |
| 13 | 25.05 | 15 |
| 14 | 26.24 | 9 |
| 15 | 28.40 | 8 |
| 16 | 35.08 | 11 |

Data generated in vitro and in animal studies support a role for TARP γ8 dependent AMPA receptor antagonists, and the compounds of the present invention in particular, in the treatment of seizures. Specifically it is found that the compound of the present invention selectively antagonizes TARP γ8 dependent AMPA receptors with high potency and protects against seizures in the rat pentylenetetrazole (PTZ)-induced seizure model. The compound of the present invention also demonstrates analgesic activity in the formalin induced pain model in mice.

To further demonstrate the characteristics of the compounds of the present invention, compounds may be run in the following in vitro and in vivo assays:

FLIPR Antagonist Functional Assay

The TARP subtype-selectivity of AMPA receptor antagonist compounds is demonstrated by comparing activities of compounds at AMPA GluA1 flop isoform receptor subunits co-expressed in CHO-S cells with either a hippocampal enriched TARP (TARP γ-8), or a cerebellar enriched TARP (TARP γ-2). TARP dependency of the AMPA receptor antagonist compounds is demonstrated by comparing the above activities with activity at AMPA GluA1 flip isoform receptor subunits expressed in CHO-S cells in the absence of a co-expressed TARP.

Briefly, CHO-S (Invitrogen) cells are grown in suspension in 50/50 custom media to a density of 1×10$^7$ cells/ml. (50/50 custom media is a low calcium media made as a 1:1 (v/v) mixture of CD CHO media (Gibco #10743) and a custom complete media. The custom complete media is made by adding 0.40 mg/L tropolone, 5.00 mg/L insulin, 20 mM HEPES, and 0.075% Pluronic® F68 to a custom basal media having the following formula: (values as mg/L unless otherwise specified) 11.01 anhydrous calcium chloride, 0.050 ferric nitrate-9$H_2O$, 0.420 ferrous sulfate-7$H_2O$, 28.64 anhydrous magnesium chloride, 48.84 anhydrous magnesium sulfate, 312.14 KCl, 5505.96 NaCl, 62.57 monobasic sodium phosphate, 71.28 anhydrous dibasic sodium phosphate, 0.432 zinc sulfate-7$H_2O$, 10.0 ethanolamine HCl, 6000 D-glucose (dextrose), 0.210 DL lipoic acid thioctic, 0.081 putrescine 2 HCl, 4.78 sodium hypoxanthine, 220.24 sodium pyruvate, 0.730 thymidine, 8.90 L-alanine, 211.23 L-arginine HCl, 15.02 L-asparagine $H_2O$, 13,31 L-aspartic acid, 62.67 cystine 2 HCl, 7.360 L-glutamic acid, 146.16 L-Glutamine, 30.0 gylicine, 42.04 L-histidine HCl 2 H₂O, 105.11 L-isoluecine, 105.11 L-luecine, 146.16 L-lysine HCl, 30.03 L-methionine, 66.07 L-phenylalanine, 17.27 L-proline, 42.04 L-serine, 95.1 L-threonine, 16.02 L-typtophan, 104.11 L-tyrosine disodium salt, 94.1 L-valine, 8.99 choline chloride, 4.00 folic acid, 12.611 inositol, 4.00 niacinamide, 4.00 pyridoxal HCl, 0.031 pyridoxine HCl, 0.400 riboflavin, 4.00 sodium pantothenate, 4.00 thiamine HCl, 0.680 vitamin B12, and 2200 sodium bicarbonate.) Cells are centrifuged at 1000×g for 15 min. and resuspended in fresh 50/50 custom media at $2 \times 10^6$ cells/ml. For batch transfection, 2 mg of total DNA(s) is used for each liter of cells. For GluA1-γ8 transfection of CHO-S cells, human GluA1Qflop-Cacng8-pBudCE4.1 DNA (Qiagen) and human EAAT3 pAN104 DNA (Qiagen, a glutamine transporter) are mixed in a ratio of 2:3. For GluA1-γ2 transfection of CHO-S cells, human GluA1Qflop-Cacng2-pBudCE4.1 (Qiagen) is used. For GluA1flip transfection of CHO-S cells, human GluA1flip pcDNA3.1 DNA (Qiagen) is used. DNA(s) and FreeStyle™ MAX Reagent (Invitrogen cat#16447-500) are added to basal custom media (see above) in the proportions of 10 μg total DNA: 10 μl FreeStyle™ MAX Reagent: 1 ml media, to form a DNA complex. After 15 min., an appropriate volume (20% v/v) of DNA complex is added to the prepared cell culture. Transiently transfected CHO-S cells are harvested after 48 hours and frozen in aliquots for later use. The function and pharmacology of AMPA receptors in transfected cells is verified in both freshly prepared and thawed aliquots of cells.

Frozen transfected CHO-S cells expressing AMPA receptors are thawed and plated in Dulbecco's Modified Eagle Media (DMEM media) (Gibco, cat#11960) containing 5% dialyzed Fetal Bovine Serum (Gibco, cat#26400-036) and 20 mM HEPES at 50,000 cells per well in 384-well Poly-D-lysine coated plates (Becton Dickinson, cat#354663) and cultured overnight at 37° C. On the day of an experiment, two fluorescence dye loading buffers are prepared. Fluo-4 AM dye loading buffer consists of 5 μM Fluo-4 AM dye (Molecular Probes, cat#F-14202) in Hank's Balanced Salt Solution (HBSS) containing 20 mM HEPES (pH 7.4), 2.5 mM probenecid (Sigma, cat#P8761, inhibits cellular transporters from pumping the dye out), and 5 nM Pluronic® F-127 (Molecular probes, cat#P3000MP). Fluo-4 NW dye loading buffer is prepared by adding 100 ml of HBSS containing 20 mM HEPES (pH 7.4) and 2.5 mM probenecid to one bottle of Fluo-4 NW dye (Molecular Probes, high throughput pack, cat#F36205). Cultured GluA1-γ8 and GluA1-γ2 CHO-S cells are loaded with Fluo-4 AM dye loading buffer and incubated at 22° C. for 2 hr. GluA1flip CHO-S cells are loaded with Fluo-4 NW dye loading buffer and incubated at 37° C. for 30 min. followed by an additional 90 mM incubation at 22° C. Prior to initiation of exposure of cells to compounds, the dye loading buffer in the cell plate is removed and fresh assay buffer is added. Assay buffer consists of HBSS with 20 mM HEPES (pH 7.4), 2.5 mM probenecid and 4 mM CaCl₂. The assay is initiated by addition of compounds followed by stimulation of cells with glutamate (final concentration=45 μM) and cyclothiazide (CTZ, final concentration=20 μM) in assay buffer. Changes in intracellular [Ca++] are kinetically recorded by a fluorescence imaging plate reader (FLIPR) Inhibition of the effect of glutamate by test compounds is expressed as a percentage of the responses stimulated by glutamate plus CTZ in the presence of test compounds to the effect seen in the absence of compounds. Relative $IC_{50}$s are calculated using a 4-parameter nonlinear logistic equation. Compounds are similarly evaluated using CHO-S cells expressing GluA1flip alone or GluA1flop-γ2 to confirm TARP-dependent and TARP-selective activity.

The compound of Example 2 is assayed essentially as described above and is found to inhibit glutamate plus CTZ activation of TARP γ8 dependent GluA1 flop receptors at about 85.6±0.7% (average±SEM, n=9), with an $IC_{50}$ of 74.5±17.8 nM (average±SEM, n=9), but did not inhibit flip isoform devoid of TARP, nor TARP γ2 dependent GluA1 flop receptors ($IC_{50}$'s>assay limit of 9260 nM).

Therefore, physiologically relevant doses of the compounds of the invention are expected to provide substantial inhibition of TARP γ8 AMPA receptors in vivo, while not substantially interacting with other physiologically relevant receptors, as for example TARP independent receptors or TARP γ2 dependent receptors, and thus may be useful in the treatment of seizure while avoiding undesired effects associated with non-TARP-dependent AMPA receptor antagonists.

Rat Pentylenetetrazole (PTZ)-Induced Seizure Model:

Male Sprague Dawley rats (from Harlan Sprague Dawley. Indianapolis, Ind.), weighing 90-110 grams at time of test, are housed 5 per cage with ad libitum food and water in a large colony room with a standard light cycle (lights on 6 am, lights off 6 pm). Animals are maintained in the colony room for at least 3 days before testing Animals are moved to a quiet room 1 hr. prior to the start of the test. Animals are used only once.

Animals are removed and dosed with test compound or vehicle (5% DMSO, 10% acacia and 0.05% Dow Corning® 1510-US antifoam), p.o., 10 mL/Kg, and returned to their home cage. Twenty five min. after dosing, animals are placed onto a screen and the screen is inverted 180 degrees to test for motor impairment. The animals are scored 60 sec. after inversion as follows: 0 if the animal climbs over the screen; 1 if the animal is hanging onto the bottom of the screen; 2 if the animal has fallen off the screen. After completing the screen test, animals are dosed S.C. with 35 mg/kg PTZ in saline in a volume of 1 ml/kg. The animals are then placed in an observation cage and observed for 30 min. post PTZ. Clonus is defined as clonic seizure of fore- and/or hindlimbs during which the rat demonstrates loss of righting. Tonic seizure is defined as loss of righting with tonic hindlimb extension. Lethality during the observation period is also recorded. Animals are scored according to the presence of a specific seizure type at any time during the observation period. Data are reported as the number of animals having a given seizure type (ex. 4/5 clonic seizures means 4 out of 5 animals exhibited at least one clonic seizure of any duration at any time during the observation period).

The compound of Example 2 is tested essentially as described above in the dose range of 1-10 mg/Kg and is found to protect rats against PTZ induced seizures with an estimated $ED_{50}$ of 1.74 mg/Kg and 100% protection at the 10 mg/Kg dose, without any observed motor impairment as measured by the inverted screen test. This data indicates that the compound of Example 2 is efficacious in a rat seizure model and, therefore, that compounds of the invention may be useful in the treatment of seizure while avoiding undesired effects associated with non-TARP-dependent AMPA receptor antagonists.

Manual Formalin Induced Pain Model

The manual formalin induced pain model is well known for screening compounds for analgesic properties (Mogil J. S. et al., Heritability of nociception I: Responses of 11 inbred mouse strains on 12 measures of nociception. Pain 80 (1999) 67-82). The assay is performed in Plexiglas® boxes approx. 10 cm×10 cm×10 cm in size. A minor placed at the back of the cage allows the unhindered observation of the formalin injected paw. Non-fasted male mice (Harlan (HSD) CD1-Icr) are placed individually in the cubicles at least 60 min. prior to the experiment. All testing is conducted between 08:00 and 16:00 hr. and the testing room temperature is maintained at 21-23° C. Multiple doses of test compound (3, 10 and 30 mg/kg), vehicle (5% DMSO in 10% Acacia, 0.05% antifoam), and a positive control (tramadol 80 mg/kg in 1% HEC, 0.25% Tween 80, 0.05% antifoam) are peripherally administered (p.o.) at varying times before the formalin challenge. Formalin (20 μL of a 5% solution in 0.9% saline) is injected subcutaneously into the plantar surface of the left hind paw with a 27 gauge needle. Observation starts immediately after the formalin injection. Formalin induced pain is quantified by recording the number of seconds each licking event lasts in 5 min. intervals. The pain scoring is measured for 60 min. after the formalin injection. Two phases of pain behavior are observed as previously described (Wheeler-Aceto, H., Porreca, F. and Cowan, A., The rat paw formalin test: comparison of noxious agents, Pain 40 (1990) 229-238.). The early phase starts immediately after the formalin injection and lasts approximately 5 min., followed by the late phase that starts between minutes 10-15 with a maximum response typically observed around 25-40 min after the formalin injection. After the 60 min observation period, animals are sacrificed with $CO_2$ followed by cervical dislocation. Of the different scoring parameters reported for the formalin test, the total time spent licking and biting the injected paw is considered to be most relevant. (Abbott et al., *The formalin test: scoring properties of the first and second phases of the pain response in rats*, Pain 60 (1995) 91-102; Coderre et al., *The formalin test: a validation of the weighted-scores method of the behavioral pain rating*, Pain 54 (1993) 43-50).) The early phase score is the sum of time spent licking (seconds) from time 0 to 5 min. The late phase score is obtained by adding the total number of seconds spent licking from minute 15 to min. 55 of the observation period. Data are presented as means with standard errors of means (±SEM). Data are evaluated by one-way analysis of variance (ANOVA) and the appropriate contrasts analyzed by Dunnett "t" test for two sided comparisons. Differences are considered to be significant if the P-value is less than 0.05. (Abbott, supra.; Coderre, supra.; and Wheeler-Aceto, supra.)

The compound of Example 2 is tested essentially as described above and is found to significantly reduce pain behavior with an $ED_{50}$ of 2.61 mg/kg derived from the following dose responses:

| Dose (mg/kg p.o.) | % reduction in total time licking | S.E.M. |
|---|---|---|
| 30 | 90.0 | 3.4% |
| 10 | 80.4 | 8.6% |
| 3 | 53.9 | 7.2% |

Therefore, compounds of the invention may be useful in the treatment of pain.

While it is possible to administer compounds employed in the methods of this invention directly without any formulation, the compounds are usually administered in the form of pharmaceutical compositions comprising the compound of Formula I, or a pharmaceutically acceptable salt thereof, as an active ingredient and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., 21st ed., Lippincott Williams & Wilkins Co., 2005).

The compositions are preferably formulated in a unit dosage form, each dosage containing from about 25 to about 1000 mg, more usually about 50 to about 500 mg, as for example about 100 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.3 mg/kg to about 15 mg/kg, more usually from about 0.7 mg/kg to about 7.5 mg/kg, and as for example about 1.5 mg/kg of body weight. In some instances dosage levels below the lower limit of the aforesaid range may be more than adequate, while in other cases still larger doses may be employed without causing any harmful side effect, and therefore the above dosage ranges are not intended to limit the scope of the invention in any way. It may also be advantageous to administer the daily dose in parts over the course of each day (e.g. ½ dose twice a day or ⅓ dose three times a day). It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

It is contemplated that the compound of the invention, or a pharmaceutically acceptable salt thereof, as for example in a pharmaceutical composition of the invention, will be used to treat seizures by chronic administration to prevent such seizures and/or by acute administration to control or stop ongoing seizures.

We claim:

1. A compound of the formula

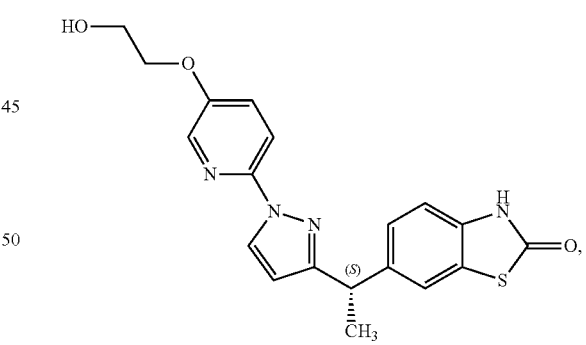

or a pharmaceutically acceptable salt thereof.

2. A compound according to claim 1 which is 6-((S)-1-{1-[5-(2-hydroxy-ethoxy)-pyridin-2-yl]-1H-pyrazol-3-yl}-ethyl)-3H-1,3-benzothiazol-2-one.

3. A pharmaceutical composition comprising 6-((S)-1-{1-[5-(2-hydroxy-ethoxy)-pyridin-2-yl]-1H-pyrazol-3-yl}-ethyl)-3H-1,3-benzothiazol-2-one, or a pharmaceutically acceptable salt thereof, and one or more pharmaceutically acceptable carriers, diluents, or excipients.

4. A method of treating seizures in a mammal with epilepsy comprising administering to a mammal in need of such treatment an effective amount of a compound of the formula

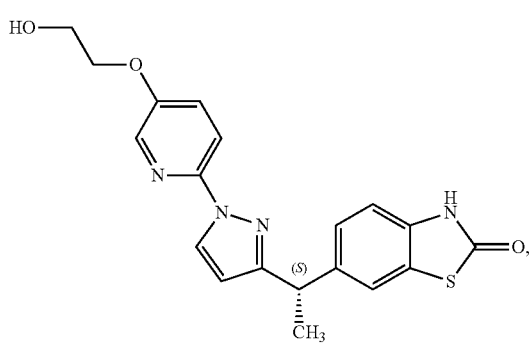

or a pharmaceutically acceptable salt thereof.

5. The method of claim 4 wherein the mammal is a human.

6. The method of claim 4 wherein the seizures are simple or complex partial onset seizures.

7. The method of claim 6 wherein the mammal is a human.

8. The method of claim 4 wherein the seizures are primary or secondary generalized seizures.

9. The method of claim 8 wherein the mammal is a human.

10. The method of claim 4 further comprising the simultaneous, separate, or sequential administration of another anti-epileptic drug.

11. The method of claim 10 wherein the other anti-epileptic is levetiracetam, gabapentin, topiramate, or carbamazepine.

12. A method of treating nociceptive pain in a mammal comprising administering to a mammal in need of such treatment an effective amount of a compound of the formula

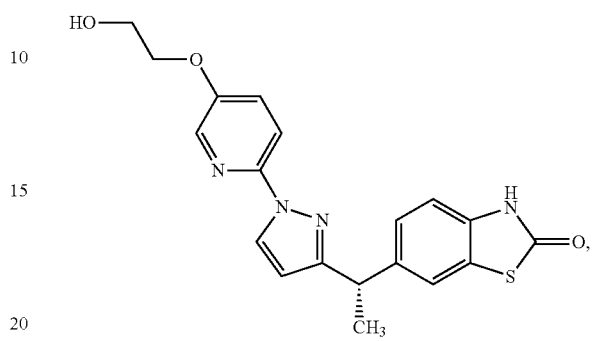

or a pharmaceutically acceptable salt thereof.

13. The method of claim 12 where the mammal is a human.

* * * * *

UNITED STATES PATENT AND TRADEMARK OFFICE
CERTIFICATE OF CORRECTION

PATENT NO. : 8,765,960 B2  
APPLICATION NO. : 14/084683  
DATED : July 1, 2014  
INVENTOR(S) : Jon Kevin Reel and Warren Jaye Porter It is certified that error appears in the above-identified patent and that said Letters Patent is hereby corrected as shown below:

Title Page, Item (54), and in the Specification, Column 1, Line 1, (Title), Delete "6-((S)-1- {1" and insert -- 6-((S)-1-{1 --, therefor.

In the Claims

Column 16, Lines 7-20, Claim 12, delete

" 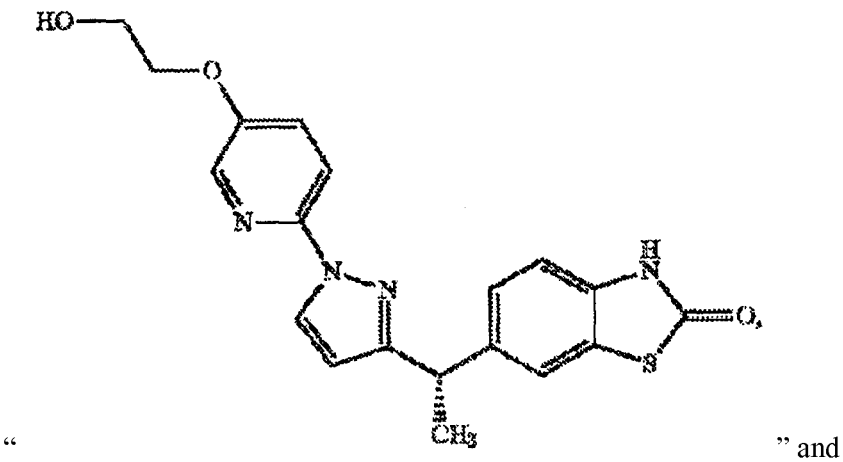 " and

Signed and Sealed this  
Ninth Day of December, 2014

Michelle K. Lee  
*Deputy Director of the United States Patent and Trademark Office*

CERTIFICATE OF CORRECTION (continued)
U.S. Pat. No. 8,765,960 B2 insert -- 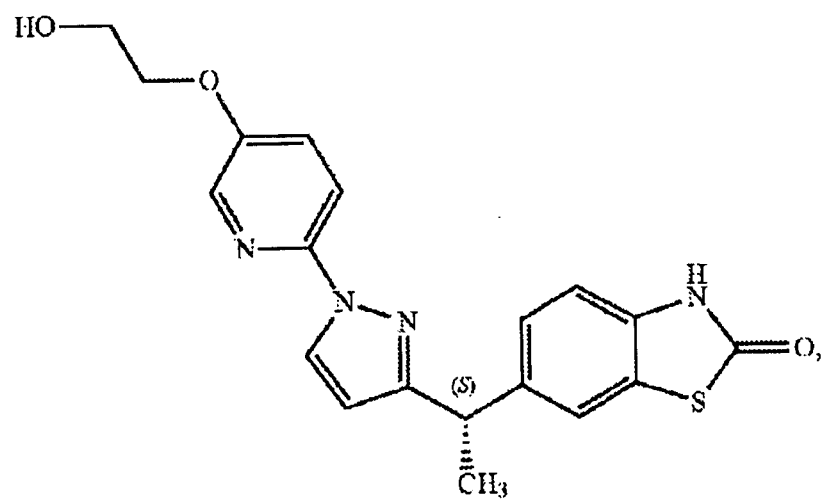 --